US010849618B2

(12) United States Patent
Cheney et al.

(10) Patent No.: US 10,849,618 B2
(45) Date of Patent: Dec. 1, 2020

(54) METHOD AND APPARATUS FOR LOADING AND IMPLANTING A SHAPE MEMORY IMPLANT

(71) Applicant: BioMedical Enterprises, Inc., San Antonio, TX (US)

(72) Inventors: Daniel F. Cheney, San Antonio, TX (US); Adam T. Knight, San Antonio, TX (US)

(73) Assignee: BioMedical Enterprises, Inc., San Antonio, TX (US)

(*) Notice: Subject to any disclaimer, the term of this patent is extended or adjusted under 35 U.S.C. 154(b) by 93 days.

(21) Appl. No.: 16/351,840

(22) Filed: Mar. 13, 2019

(65) Prior Publication Data

US 2019/0209168 A1 Jul. 11, 2019

Related U.S. Application Data

(60) Division of application No. 14/944,710, filed on Nov. 18, 2015, now Pat. No. 10,456,130, which is a continuation-in-part of application No. 14/271,563, filed on May 7, 2014, now Pat. No. 9,585,656.

(60) Provisional application No. 62/086,388, filed on Dec. 2, 2014.

(51) Int. Cl.
*A61B 17/064* (2006.01)

(52) U.S. Cl.
CPC .. *A61B 17/0642* (2013.01); *A61B 2017/0641* (2013.01); *A61B 2017/0645* (2013.01)

(58) Field of Classification Search
CPC .............. A61B 17/064; A61B 17/0642; A61B 17/0644; A61B 2017/0641; A61B 2017/0645; A61B 2017/0646
See application file for complete search history.

(56) References Cited

U.S. PATENT DOCUMENTS

| 1,106,241 A | 8/1914 | Richardson |
| 2,544,492 A | 3/1947 | Downing |
| 3,939,828 A | 2/1976 | Mohr et al. |
| 3,960,147 A | 6/1976 | Murray |
| 4,269,180 A | 5/1981 | Dall et al. |

(Continued)

FOREIGN PATENT DOCUMENTS

| EP | 0682920 B1 | 2/1995 |
| EP | 0826340 A2 | 3/1998 |

(Continued)

OTHER PUBLICATIONS

4-Fusion Shape Memory Implant Training Slide Images, Memometal, Inc., 2008.

(Continued)

*Primary Examiner* — Eric S Gibson
(74) *Attorney, Agent, or Firm* — Christopher L. Makay

(57) ABSTRACT

An implant insertion device is adapted for use with a shape memory implant. The shape memory implant includes a bridge interconnecting first, second, and third legs. The shape memory implant is movable between a first shape in which at least the first leg is substantially non-parallel and a second shape in which at least the first leg is substantially parallel. The implant insertion device engages the shape memory implant to maintain the shape memory implant in its second shape until the delivery of the shape memory implant into tissue or bone.

2 Claims, 14 Drawing Sheets

(56) References Cited

U.S. PATENT DOCUMENTS

| | | | |
|---|---|---|---|
| 4,438,769 A * | 3/1984 | Pratt | A61B 17/0642 227/147 |
| 4,485,816 A | 12/1984 | Krumme | |
| 4,526,174 A | 7/1985 | Froehlich | |
| 4,570,623 A | 2/1986 | Ellison et al. | |
| 4,592,346 A | 6/1986 | Jurgutis | |
| 4,608,972 A | 9/1986 | Small | |
| 4,665,906 A | 5/1987 | Jervis | |
| 4,713,077 A | 12/1987 | Small | |
| 4,869,243 A | 9/1989 | Huene | |
| 5,067,957 A | 11/1991 | Jervis | |
| 5,112,336 A | 5/1992 | Krevolin et al. | |
| 5,163,557 A | 11/1992 | Sokolowski | |
| 5,171,252 A | 12/1992 | Friedland | |
| 5,246,443 A | 9/1993 | Mai | |
| 5,357,732 A | 10/1994 | Markle et al. | |
| 5,425,489 A | 6/1995 | Shichman et al. | |
| 5,474,557 A * | 12/1995 | Mai | A61B 17/0642 606/219 |
| 5,478,354 A * | 12/1995 | Tovey | A61B 17/0057 411/457 |
| 5,769,856 A | 6/1998 | Dong et al. | |
| 5,779,707 A | 7/1998 | Bertholet et al. | |
| 5,785,713 A | 7/1998 | Jobe | |
| 5,976,159 A * | 11/1999 | Bolduc | A61B 17/064 606/104 |
| 6,001,110 A | 12/1999 | Adams | |
| 6,187,009 B1 | 2/2001 | Herzog et al. | |
| 6,268,589 B1 | 7/2001 | Flot | |
| 6,323,461 B2 | 11/2001 | Flot | |
| 6,412,639 B1 | 7/2002 | Hickey | |
| 6,607,542 B1 | 8/2003 | Wild | |
| 6,685,708 B2 | 2/2004 | Monassevitch et al. | |
| 6,783,531 B2 | 8/2004 | Allen | |
| 6,827,723 B2 | 12/2004 | Carson | |
| 7,240,677 B2 | 7/2007 | Fox | |
| 7,344,539 B2 | 3/2008 | Serhan et al. | |
| 7,428,807 B2 | 9/2008 | Vander Bush et al. | |
| 7,556,647 B2 | 7/2009 | Drews et al. | |
| 7,678,115 B2 | 3/2010 | D'Alessio et al. | |
| 7,867,265 B2 | 1/2011 | Beutter | |
| 8,057,490 B2 | 11/2011 | Harris | |
| 8,114,138 B2 | 2/2012 | Nehls | |
| 8,118,952 B2 | 2/2012 | Gall et al. | |
| 8,137,351 B2 * | 3/2012 | Prandi | A61B 17/0682 606/75 |
| 8,191,220 B2 | 6/2012 | Magnuson et al. | |
| 8,211,109 B2 * | 7/2012 | Groiso | A61B 17/0642 606/75 |
| D669,984 S | 10/2012 | Cheney et al. | |
| D669,985 S | 10/2012 | Cheney et al. | |
| D676,962 S | 2/2013 | Cheney et al. | |
| 8,584,853 B2 | 11/2013 | Knight et al. | |
| 8,596,514 B2 * | 12/2013 | Miller | A61B 17/0642 227/175.1 |
| 9,585,656 B2 * | 3/2017 | Taber | A61B 17/0642 |
| 9,855,036 B2 * | 1/2018 | Palmer | A61B 17/0642 |
| 9,931,115 B2 * | 4/2018 | Morgan | A61B 17/7291 |
| 10,456,130 B2 * | 10/2019 | Cheney | A61B 17/0642 |
| 2004/0097970 A1 | 5/2004 | Hughett | |
| 2005/0033430 A1 | 2/2005 | Powers et al. | |
| 2005/0043757 A1 | 2/2005 | Arad et al. | |
| 2005/0080454 A1 * | 4/2005 | Drews | A61B 17/064 606/221 |
| 2005/0009660 A1 | 5/2005 | Allen | |
| 2005/0107807 A1 | 5/2005 | Nakao | |
| 2005/0113832 A1 | 5/2005 | Molz et al. | |
| 2005/0143749 A1 | 6/2005 | Zalenski et al. | |
| 2006/0106388 A1 | 5/2006 | Lococo | |
| 2006/0229627 A1 | 10/2006 | Hunt et al. | |
| 2007/0118141 A1 | 5/2007 | Marchyn et al. | |
| 2007/0118224 A1 | 5/2007 | Shah et al. | |
| 2008/0065153 A1 * | 3/2008 | Allard | A61B 17/0644 606/219 |
| 2008/0110957 A1 * | 5/2008 | McBride | A61B 17/068 227/175.1 |
| 2008/0319443 A1 * | 12/2008 | Focht | A61B 17/0642 606/75 |
| 2009/0062800 A1 | 3/2009 | Shano | |
| 2009/0062806 A1 | 3/2009 | Scott et al. | |
| 2009/0216285 A1 | 8/2009 | Ek et al. | |
| 2009/0272786 A1 | 11/2009 | Zeiner et al. | |
| 2010/0133316 A1 * | 6/2010 | Lizee | A61B 17/0642 227/175.1 |
| 2010/0191258 A1 | 7/2010 | Harris et al. | |
| 2010/0217270 A1 | 8/2010 | Polinski et al. | |
| 2011/0093018 A1 | 4/2011 | Prasad et al. | |
| 2011/0186456 A1 | 8/2011 | Bertazzoni et al. | |
| 2011/0270327 A1 | 11/2011 | Blakemore et al. | |
| 2012/0024937 A1 | 2/2012 | Allen | |
| 2012/0085809 A1 * | 4/2012 | Milo | A61B 17/0644 227/181.1 |
| 2012/0209305 A1 | 8/2012 | Deodhar et al. | |
| 2012/0209401 A1 | 8/2012 | Euteneuer et al. | |
| 2012/0228355 A1 * | 9/2012 | Combrowski | A61B 17/1285 227/175.1 |
| 2012/0259419 A1 | 10/2012 | Brown et al. | |
| 2013/0026206 A1 | 1/2013 | Fox | |
| 2013/0026207 A1 | 1/2013 | Fox | |
| 2013/0030437 A1 | 1/2013 | Fox | |
| 2013/0030438 A1 | 1/2013 | Fox | |
| 2013/0184476 A1 | 7/2013 | Mclff et al. | |
| 2013/0231667 A1 | 9/2013 | Taylor et al. | |
| 2014/0018809 A1 | 1/2014 | Allen | |
| 2014/0097228 A1 * | 4/2014 | Taylor | A61B 17/0682 227/181.1 |
| 2014/0175157 A1 | 6/2014 | Vold et al. | |
| 2014/0276830 A1 | 9/2014 | Cheney | |
| 2014/0277467 A1 | 9/2014 | Hibri et al. | |
| 2014/0277516 A1 * | 9/2014 | Miller | A61B 17/0642 623/18.11 |
| 2014/0358187 A1 * | 12/2014 | Taber | A61B 17/0682 606/86 R |
| 2015/0133940 A1 * | 5/2015 | Palmer | A61B 17/7266 606/75 |
| 2015/0257801 A1 | 9/2015 | Palmer et al. | |
| 2016/0015384 A1 | 1/2016 | Roedl et al. | |
| 2016/0066907 A1 * | 3/2016 | Cheney | A61B 17/0642 606/75 |
| 2016/0074037 A1 | 3/2016 | Cheney et al. | |
| 2016/0199060 A1 * | 7/2016 | Morgan | A61B 17/068 227/175.1 |
| 2016/0235460 A1 * | 8/2016 | Wahl | A61B 17/0682 |
| 2017/0000482 A1 * | 1/2017 | Averous | A61B 17/0642 |
| 2017/0065275 A1 * | 3/2017 | Cheney | A61B 17/0642 |
| 2017/0281157 A1 * | 10/2017 | Hartdegen | A61B 17/8052 |
| 2019/0209168 A1 * | 7/2019 | Cheney | A61B 17/0642 |

FOREIGN PATENT DOCUMENTS

| | | | |
|---|---|---|---|
| EP | 0857462 A1 | 12/2007 | |
| EP | 1870042 A1 | 12/2007 | |
| FR | 2874166 A1 | 2/2006 | |
| WO | 1992017122 A2 | 10/1992 | |
| WO | 2008129061 A1 | 10/2008 | |
| WO | 2011006081 A1 | 1/2011 | |
| WO | 2013055824 A1 | 4/2013 | |

OTHER PUBLICATIONS

4-Fusion Shape Memory Implant Brochure, Memometal, Inc., Jun. 23, 2009.

MemoGraph Brochure, M.B.A. (Memory Biological Application), Parc Club de Nancy de Brabois, Batiment B11, 4 allee Vincennes, 54500 Vandceurve, France, 1999.

OSStaple Brochure Including pictures of staple loaded in shipping block, BioMedical Enterprises, Inc., 14875 Omicron Drive, Suite 205, San Antonio, TX 78245, 2010.

E. A. Van Amerongen et al., "Four-Corner Arthrodesis Using the Quad Memory Staple," Journal of Hand Surgery (European vol. 2008) (Jan. 7, 2009).

(56) References Cited

OTHER PUBLICATIONS

U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.

T. F. Smith, "The Bone Staple: Tried and True Superhero of Bone Fixation," Educational Materials Update Chapter 41 (2010) available at www.podiatryinstitute.com/pdfs/Update 2010/2010 41.pdf.

Elevest Procedure Kit, Instructions for Use by CooperSurgical (© 2007).

Agee WristJack, Surgeon's Manual by Hand BioMechanics Labs, Inc. (© 1990-2002).

Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, the Netherlands, May 1994 (ESA SP-364, Aug. 1994).

Superelastic Fixation System Brochure, Memometal Inc., USA, Aug. 12, 2009.

Shape Memory Staple System for Arthrodesis and Skeletal Fixation of the Hand Brochure, Core Essence Orhtopaedics, Inc., 2009.

ENTact™ Septal Stapler, Product brochure by ENTrigue Surgical, Inc. (© 2009).

R. M. Sloan et al., "Orthopedic Fixation Devices," Radiographics at 823 (Sep. 1991).

J. Arthur, "Improving Operating Efficiency in Five Days," Lean Six Sigma for Hospitals, McGraw-Hill (2011).

K. Yamauchi et al. (ed.), "Shape Memory and Superelastic Alloys: Applications and Technologies" (2011).

BioResearch Innovations (BRI), "Memodyn Compression Staple," FDA 510(K) disclosure (Jan. 2004).

G. C. Taylor et al., "Complications of Internal Fixation," Podiatry Institute Educational Materials Update Chapter 79 (1992).

Wright Medical Technology, Inc., "Charlotte Compression Staple as described by Robert Anderson, MD; Bruce Cohen, MD; and W. Hodges Davis, MD" (2007).

A. A. Weinbroum et al., "Efficiency of the Operating Room Suite," American Journal of Surgery 244-250 (2003).

G. G. Porto, "Safety by Design: Ten Lessons From Human Factors Research," Journal of Healthcare Risk Management 43-50 (Fall 2011).

Russell, Scott M., Design Considerations for Nitinol Bone Staples, Journals of Materials Engineering and Performance, vol. 18(5-6), Aug. 2009, USA.

* cited by examiner

METHOD AND APPARATUS FOR LOADING AND IMPLANTING A SHAPE MEMORY IMPLANT

BACKGROUND OF THE INVENTION

1. Field of the Invention

The present invention relates generally to an implantation device and, more particularly, but not way of limitation, to an implantation device designed for loading with a surgical implant and for subsequent delivery of the surgical implant. The implantation device uses jaws and a slider to secure a surgical implant and allow implantation into a patient.

2. Description of the Related Art

Shape memory implants are commonly used in surgical procedures that require the reattachment or fusing of tissue or bone. Shape memory implants can be composed of shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic (recoverable) deformation, and then releases the stored mechanical energy when the constraint is removed. In these types of implants, the implants are mechanically deformed into their second shape and maintained in their second shape by instrumentation such that, upon release from the instrumentation, the implants elastically deform from their second shape into their first final shape.

In surgical procedures, the elastic property of constrained shape memory implants is used as follows. Bones that require fixating are aligned, and the shape memory implant, which has been mechanically deformed to its second shape, is maintained in instrumentation and inserted between the bones. In the second shape, the legs of the implant are generally parallel. After insertion, the shape memory implant is released from the instrumentation, whereupon the shape memory implant elastically returns to its first final shape such that the shape memory implant maintains the bones fixated together. In the first final shape, the legs of the implant are converging at the tips. Because the shape memory implant stores mechanical energy, it continuously applies force to the fixated bones as the shape memory implant transitions from the second shape to the first final shape, which aids in the healing process.

Various types of instrumentation can be used for either maintaining the shape memory implants in their second shape or moving an implant from its first final shape to a temporary second shape. Some companies used metal forceps to open and insert the shape memory implant. These forceps have to be sterilized by a hospital, and then a shape memory implant can be placed on the forceps, opened to a desired position, and used for inserting the implant. Although potentially effective, forceps require the implant to be loaded into the forceps during surgery, which might be cumbersome and time consuming. In addition, forceps might be large which could hinder implantation of the shape memory implant into a patient during surgery. It is also possible that a physician using the forceps might damage the shape memory implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Other companies use plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the implant insertion device allows the shape memory implant to be preloaded prior to surgery. However, using an implant insertion device that substantially conforms to the profile of the shape memory implant can create several problems for a surgeon. First, this type of implant insertion device often makes disengagement of the shape memory staple after implantation problematic. In particular, the shape memory implant sticks to the implant insertion device due to the frictional engagement between the shape memory implant, which is trying to compress, and the passage of the implant insertion device, resulting in a more difficult surgical procedure and the potential for a less than satisfactory fixation of tissue or bone. Second, this type of implant insertion device results in an abrupt and sudden release of stored mechanical energy as the implant is removed from the device. This type of implant insertion device provides no method by which to slowly transition the stored energy in the implant from the implant insertion device to the bones that are being fixated. Finally, this type of implant insertion device can result in entanglement during release, in which the implant legs begin to compress upon release and make extraction of this type of insertion device more difficult.

Accordingly, an instrument that constrains a shape memory implant in its second shape, allows the shape memory implant to be preloaded and sterilized prior to surgery, simplifies removal of the shape memory implant after partial implantation, and controls the rate of release of tension would be beneficial.

SUMMARY OF THE INVENTION

In accordance with the present invention, an implant insertion system includes a shape memory implant and an implant insertion device adapted for use with the shape memory implant. The shape memory implant includes a bridge interconnecting first, second, and third legs. The shape memory implant is movable between a first shape in which at least the first leg is substantially non-parallel and a second shape in which at least the first leg is substantially parallel. The implant insertion device engages the shape memory implant to maintain the shape memory implant in its second shape until the delivery of the shape memory implant into tissue or bone.

The implant insertion device includes a first insertion tool piece and a second insertion tool piece. The first insertion tool piece includes a slider slot. The first insertion tool piece terminates in a first jaw including a first tool slot adapted to receive therein a portion of the bridge of the shape memory implant. The second insertion tool piece includes a slider slot. The second insertion tool piece terminates in a second jaw including a second tool slot adapted to receive therein a portion of the bridge of the shape memory implant. The second insertion tool piece hingedly connects with the first insertion tool piece such that the first and second insertion tool pieces reside in an opposed relationship with their slider slots aligned.

The implant insertion device further includes a slider disposed in the slider slots of the first and second insertion tool pieces. The slider includes a separator disposed between the first and second insertion tool pieces. The slider moves such that the separator separates the first and second insertion tool pieces to release the shape memory implant from the first and second insertion tool pieces. The slider further moves such that the separator permits closure of the first and second insertion tool pieces. When the first and second insertion tool pieces are closed, the first and second tool slots each receive therein a portion of the bridge of the shape memory implant to maintain the shape memory implant in its second shape, the first jaw engages the first and second legs to maintain the shape memory implant in its second shape, and the second jaw engages at least the third leg to maintain the shape memory implant in its second shape. The second jaw may engage the first leg to maintain the shape memory implant in its second shape.

The first jaw includes a projection that engages the first leg to maintain the first leg substantially parallel such that the shape memory implant resides in its second shape. The first jaw further includes a projection that engages the second leg to maintain the second leg substantially parallel such that the shape memory implant resides in its second shape. The second jaw includes a projection that engages the third leg to maintain the third leg substantially parallel such that the shape memory implant resides in its second shape. The second jaw may include a projection that engages the first leg to maintain the first leg substantially parallel such that the shape memory implant resides in its second shape.

The first insertion tool piece includes a first insertion tool piece ramp, and the second insertion tool piece includes a second insertion tool piece ramp. The hinged connection between the first insertion tool piece and the second insertion tool piece places the first and second insertion tool piece ramps interior to the first and second insertion tool pieces and in an opposed relationship. When disposed in the slider slots of the first and second insertion tool pieces, the slider positions the separator between the first and second insertion tool piece ramps. The slider moves such that the separator engages the first and second insertion tool piece ramps to separate the first and second insertion tool pieces and release the shape memory implant from the first and second insertion tool pieces. The slider further moves such that the separator disengages from the first and second insertion tool piece ramps to permit closure of the first and second insertion tool pieces.

The first insertion tool piece includes a first insertion tool piece slider slot lock, and the second insertion tool piece includes a second insertion tool piece slider slot lock. The hinged connection of the first insertion tool piece with the second insertion tool piece places the first insertion tool piece slider slot lock in opposed relationship with the second insertion tool piece slider slot lock. Once the first and second insertion tool pieces are closed, the slider moves such that a slot in the slider engages the first and second insertion tool piece slider slot locks thereby locking the first insertion tool piece with the second insertion tool piece. The slider further moves such that the slot in the slider disengages from the first and second insertion tool piece slider slot locks to permit separating of the first and second insertion tool pieces.

In a method of holding a shape memory implant until the delivery of the shape memory implant into tissue or bone, a shape memory implant is provided. The shape memory implant includes a bridge interconnecting first, second, and third legs. The shape memory implant is movable between a first shape wherein the first leg is non-parallel and a second shape wherein the first leg is substantially parallel. A slider of an implant insertion device inserts between a first insertion tool piece hingedly connected to a second insertion tool piece. Responsive thereto, the first and second insertion tool pieces separate thereby opening the implant insertion device to receive the shape memory implant therein. The shape memory implant is moved into its second shape wherein the first leg is substantially parallel and placed between a first jaw of the first insertion tool piece and a second jaw of the second insertion tool piece. The slider of the implant insertion device is moved to permit closure of the first and second jaws of the first and second insertion tool pieces. When the first and second jaws are closed, a first tool slot in the first jaw and a second tool slot in the second jaw each receive therein a portion of the bridge of the shape memory implant, the first jaw engages the first and second legs to maintain the shape memory implant into its second shape wherein the first leg is substantially parallel, and the second jaw engages at least the third leg. The slider of the implant insertion device then is moved to engage the first and second insertion tool pieces to lock the first and second jaws closed about the shape memory implant into its second shape.

Once the first and second jaws are locked about the shape memory implant into its second shape, the implant insertion device is used to deliver the shape memory implant into tissue or bone. After delivering the shape memory implant into tissue or bone, the slider of the implant insertion device is moved such that the slider disengages from the first and second insertion tool pieces to unlock the first and second jaws. The slider of the implant insertion device then is moved to insert between the first and second insertion tool pieces such that the first and second insertion tool pieces separate thereby releasing the shape memory implant from the first and second jaws. Upon the release of the shape memory implant from the first and second jaws, the shape memory implant moves from its second shape wherein the first leg is substantially parallel to its first shape wherein the first leg is non-parallel.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

Figure 1:
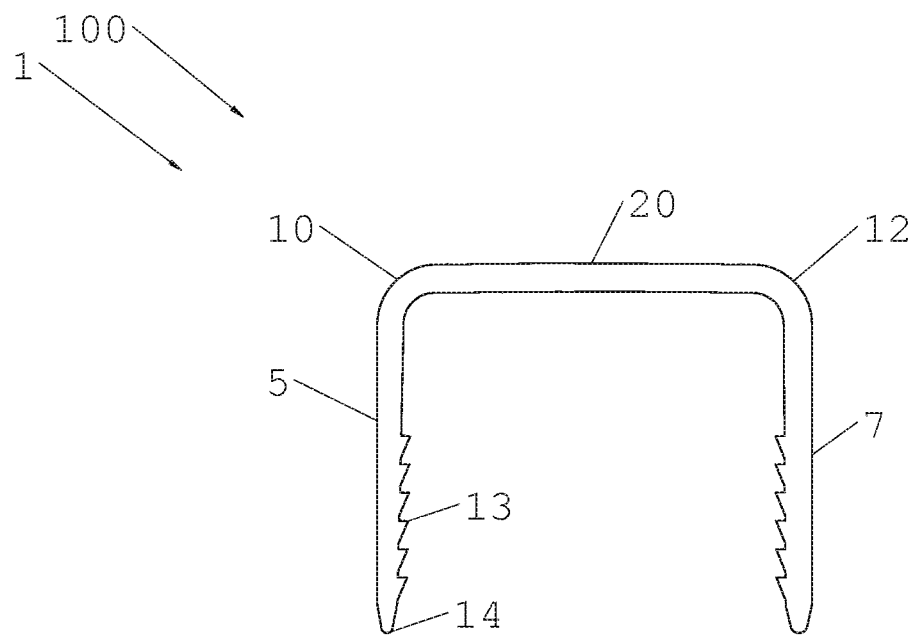
FIG. 1 is a side view of a first embodiment of an implant in a first position.
Figure 2:
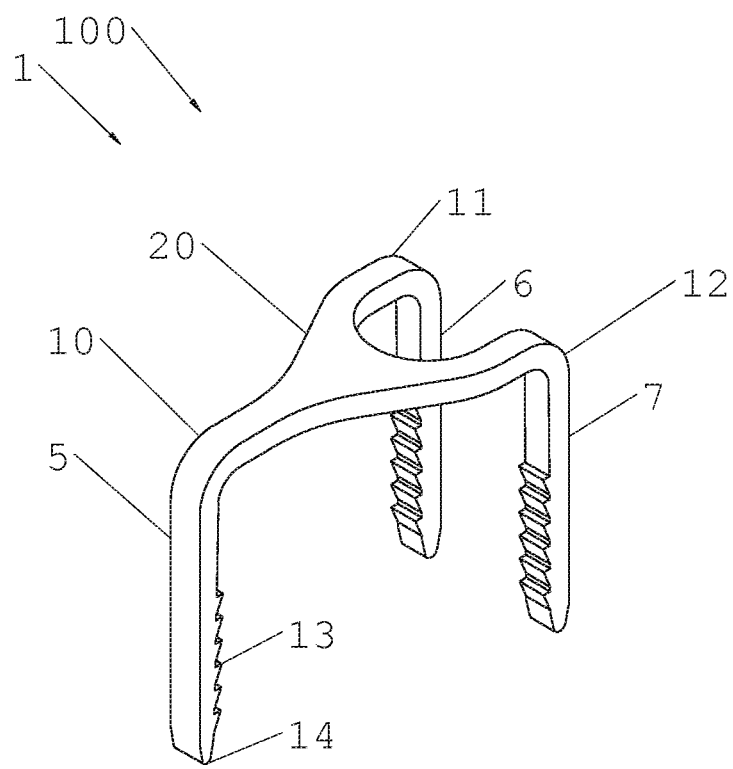
FIG. 2 is a perspective view illustrating the first embodiment of the implant in the first position.

FIGS. 1 and 2 respectively display an orthopedic implant 1 in a first position 100. Implant 1 consists of two or more legs, such as the three legs 5, 6, and 7 shown in this embodiment. Although the three legs in this embodiment form an isosceles triangle, any number of other multi-legged designs exist. Each leg is capable of penetrating into bone to anchor implant 1. Barbs on each leg, such as representative barb 13, provide resistance to movement when the implant is inserted into bone. Any number of barbs can be on each leg. Leg tip 14, which is on leg 5, but is representative of the leg tips on each leg, can be blunt or pointed for insertion into bone. Bridge 20 connects the two or more legs of implant 1. Corners 10, 11, and 12 represent the location where legs 5, 6, and 7 attach to bridge 20. Corners 10, 11, and 12 can be of any radius such that implant 1 conforms to bone when implanted. Bridge 20 is mostly flat when viewed in FIG. 1 when it is first position 100. However, there is any number of shapes for bridge 20 that will attach legs 5, 6, and 7 and conform to bone after implantation.

Implant 1 is made of an elastic material suitable for orthopedic use, such as a shape memory material. In first position 100, the legs 5, 6, and 7 of implant 1 are mostly parallel to each other, such that implant 1 can be easily inserted into holes drilled in bone. However first position 100 is not the natural shape of implant 1, and thus legs 5, 6, and 7 must be constrained either mechanically, or by chilling implant 1 until it is in the martensitic state such the legs naturally remain in first position 100.

Figure 3:
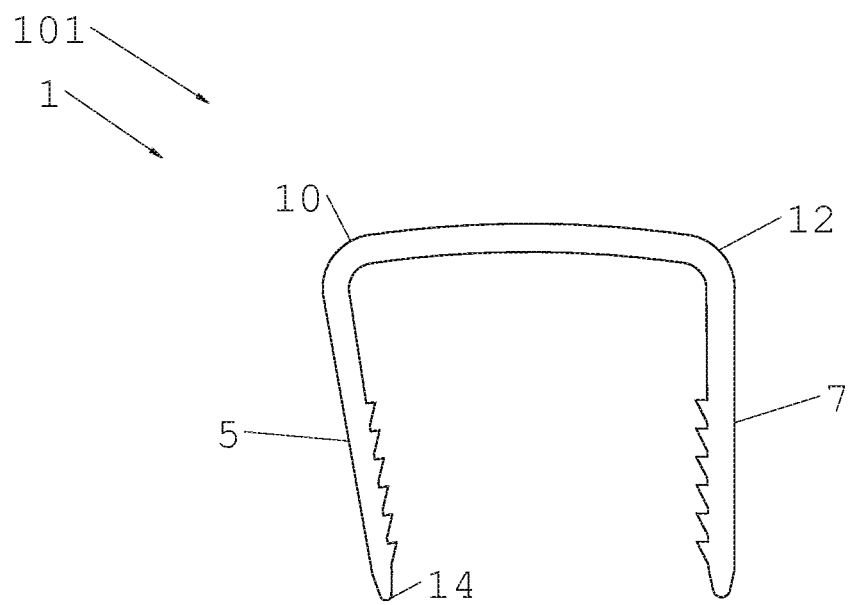
FIG. 3 is a side view of the first embodiment of the implant in a second position.
Figure 4:
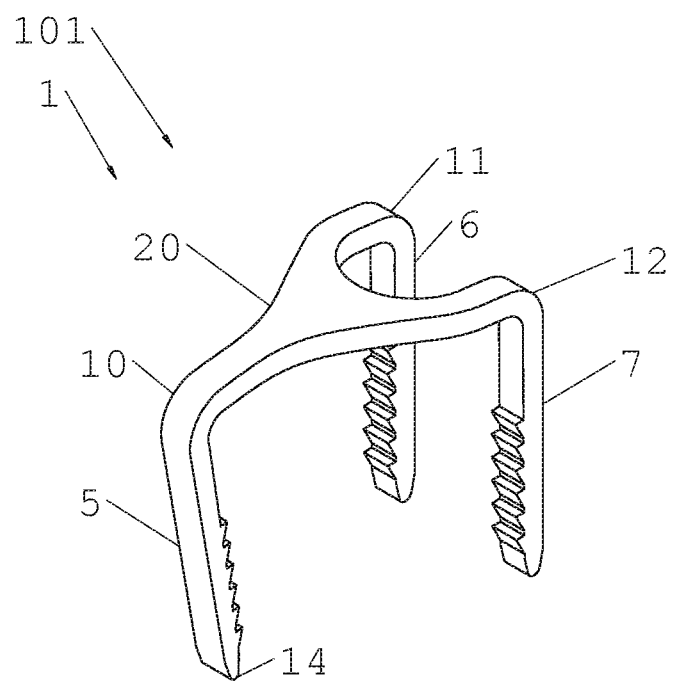
FIG. 4 is a perspective view illustrating the first embodiment of the implant in the second position.

FIGS. 3 and 4 illustrate the first embodiment of an orthopedic implant in a second position 101. Implant 1 is now in a second position in which leg 5 has moved inward due to the shape memory or superelastic property of the material near corner 10. Leg 5 is no longer parallel to legs 6 and 7. This has occurred either because a mechanical constraint of leg 5 has been removed, allowing it to swing inward, or because leg 5 was previously chilled in a deformed martensite state and now has transitioned to its natural shape in the austenite phase. Furthermore, bridge 20 has now arched due to the same reasons, so as to bring leg 5 closer to legs 6 and 7. In these two ways, implant 1 creates compression force between leg 5 and legs 6 and 7. In addition to this motion, a person familiar with the art could design implant 1 to have any number of legs, or any combination of movements. Although stationary in this embodiment, in an alternative embodiment legs 6 and 7 could move towards leg 5 or towards each other.

Figure 5:
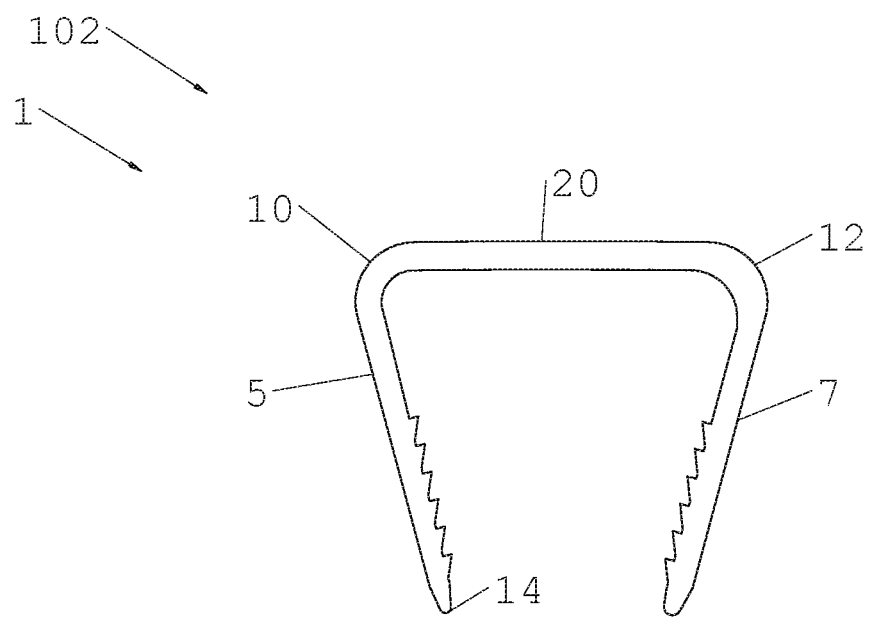
FIG. 5 is a side view of a second embodiment of the implant in a second position.
Figure 6:
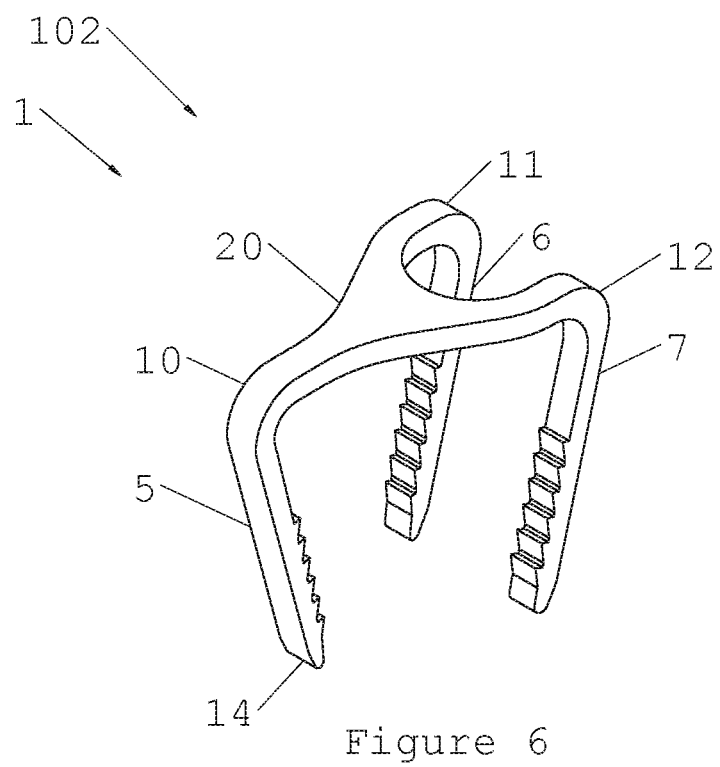
FIG. 6 is a perspective view illustrating the second embodiment of the implant in the second position.

FIGS. 5 and 6 illustrate a second embodiment of an orthopedic implant in a second position 102. In this second embodiment, implant 1 has the same features as the first embodiment, except that legs 5, 6, and 7 all move under the action of shape memory or superelasticity to non-parallel positions. The material in corners 10, 11, and 12 has now caused legs 5, 6, and 7 to move to the compressed and non-parallel positions, either due to release of a mechanical constraint on the legs or due to a phase change from chilled martensite to the austenite phase. In this way, additional compressive force is created by the legs of implant 1.

Figure 7:
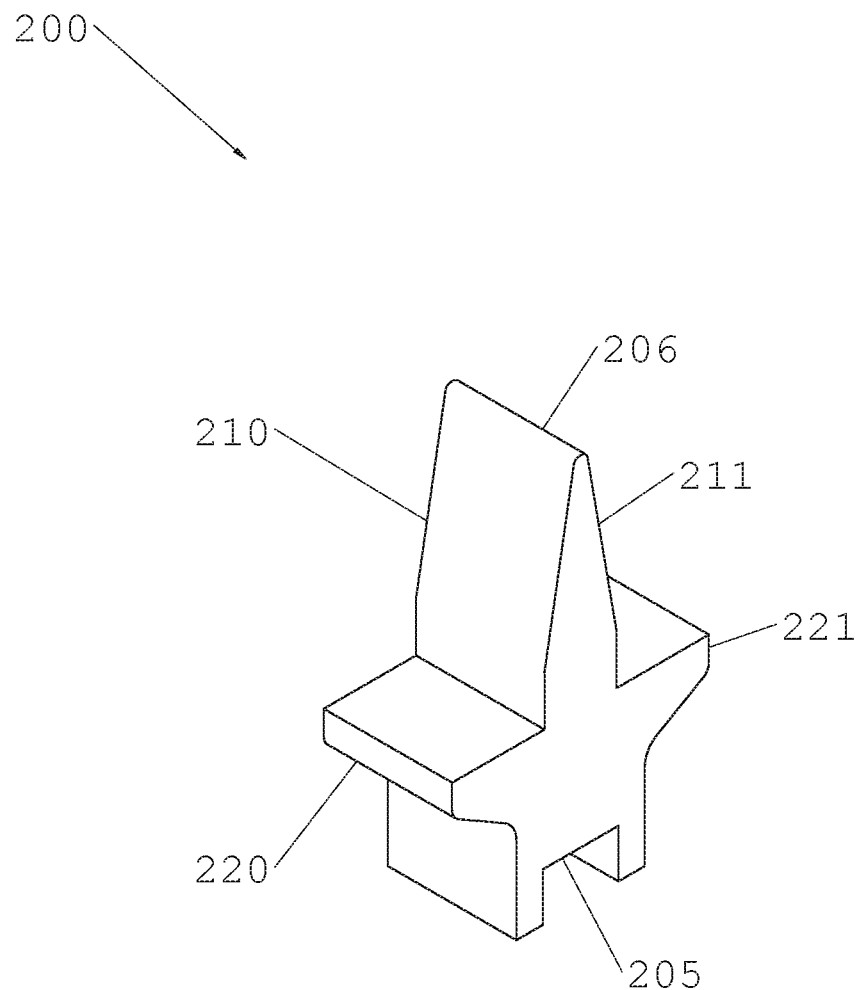
FIG. 7 is a perspective view of an insertion tool slider.

FIG. 7 is an isometric view of an insertion tool slider. Insertion tool slider 200 consists of a separator 206 defining ramps 210 and 211, finger grips 220 and 221, and slot 205. Insertion tool slider 200 can be made of any material. The purpose of insertion tool slider 200 will be more apparent in the paragraphs below, however it's general purpose is allow a physician to release a shape memory implant from an insertion tool instrument. The finger grips 220 and 221 are contoured to allow easy grasping and leverage for moving insertion tool slider 200. Slot 205 is designed to fit over mating parts that will be evident in later drawings. Ramps 210 and 211 are designed to provide separator 206 with a wedge shape that can be used to wedge two opposing pieces apart in subsequent paragraphs.

Figure 8:
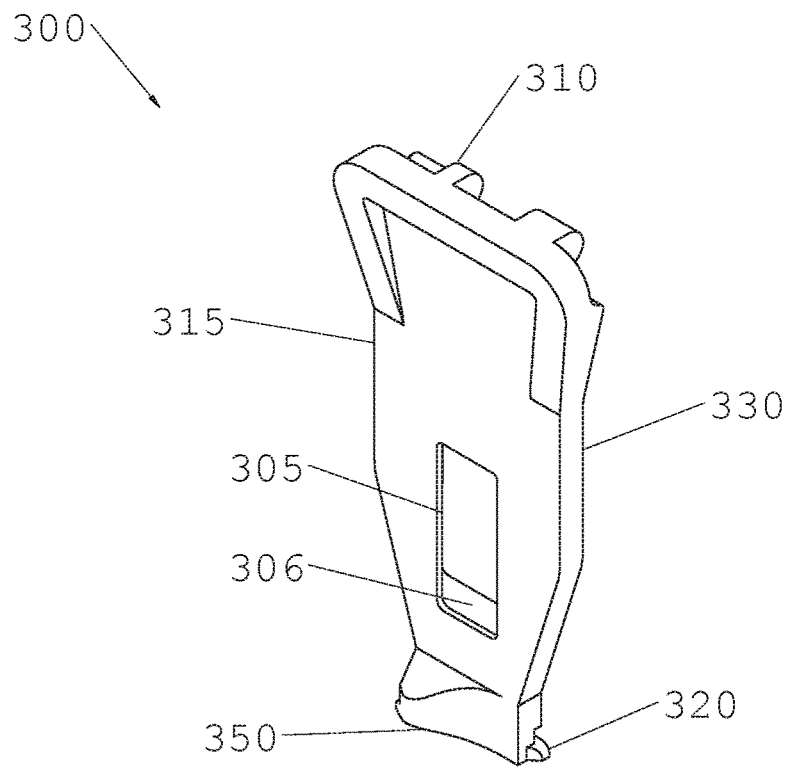
FIG. 8 is an outside view of a right insertion tool piece.
Figure 9:
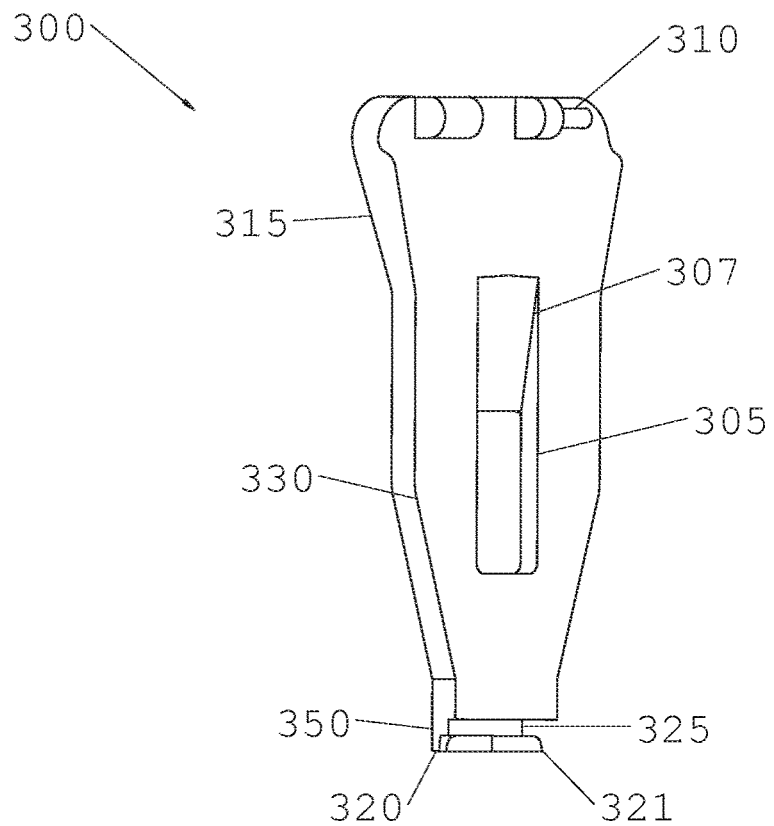
FIG. 9 is an inside view of the right insertion tool piece.

FIGS. 8 and 9 illustrate a right insertion tool piece. Right insertion tool piece 300 can be made of any material. Right insertion tool piece 300 consists of body 315, slider slot 305, slider slot lock 306, hinge 310, and additional features described below. Slider slot 305 is a window or hole in right insertion tool piece 300 that fits the dimensions of insertion tool slider 200. Slider slot lock 306 is a recessed area in right insertion tool piece 300 that also fits the dimensions of insertion tool slider 200, but in addition will allow slot 205 of insertion tool slider 200 to lock in place. This will be evident in subsequent drawings. Hinge 310 is configured to mate with a corresponding hinge on a left insertion tool piece 400, described in a subsequent drawing. Body 315 is designed to provide structural rigidity as well as ergonomic shape for a physician to hold. Right insertion tool piece 300 includes jaw 350 that is adapted to interface with an implant 1 at bridge 20 and legs 5 and 6. In particular, jaw 350 includes projections 320 and 321 that contact implant 1 at legs 5 and 6, respectively. Jaw 350 includes right insertion tool slot 325, which is only visible in FIG. 9 (inside view of the right insertion tool piece). Right insertion tool slot 325 is designed to match the shape of bridge 20 when implant 1 resides in its first position 100. Right insertion tool ramp 307, which is also only visible in FIG. 9, is a ramped section of piece 300 that will be shown later to interface with the insertion tool slider 200. Finally, right insertion tool surface 330 is a surface that can mate with a second half of an insertion tool when it is in its assembled position.

Figure 10:
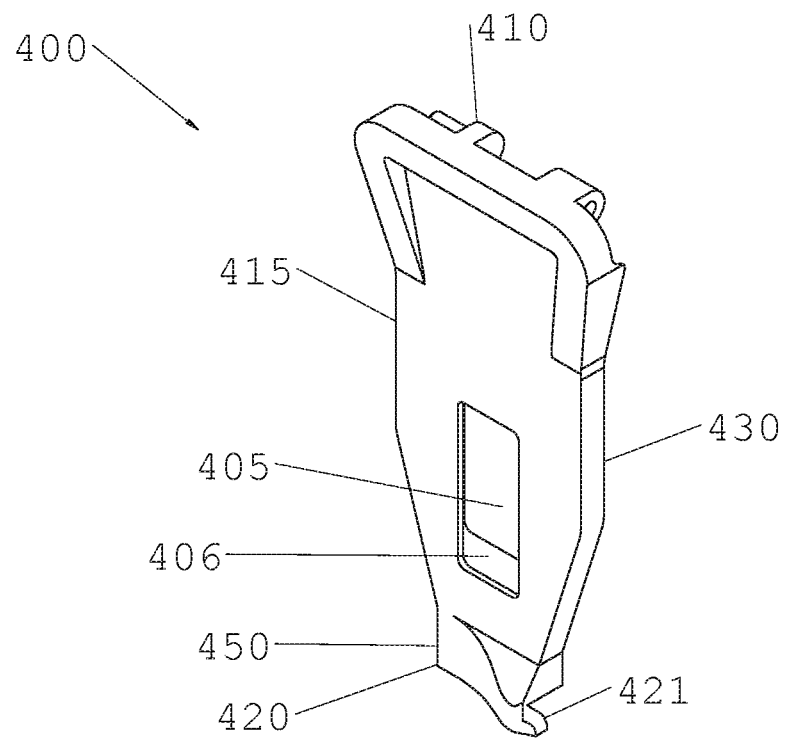
FIG. 10 is an outside view of a left insertion tool piece.
Figure 11:
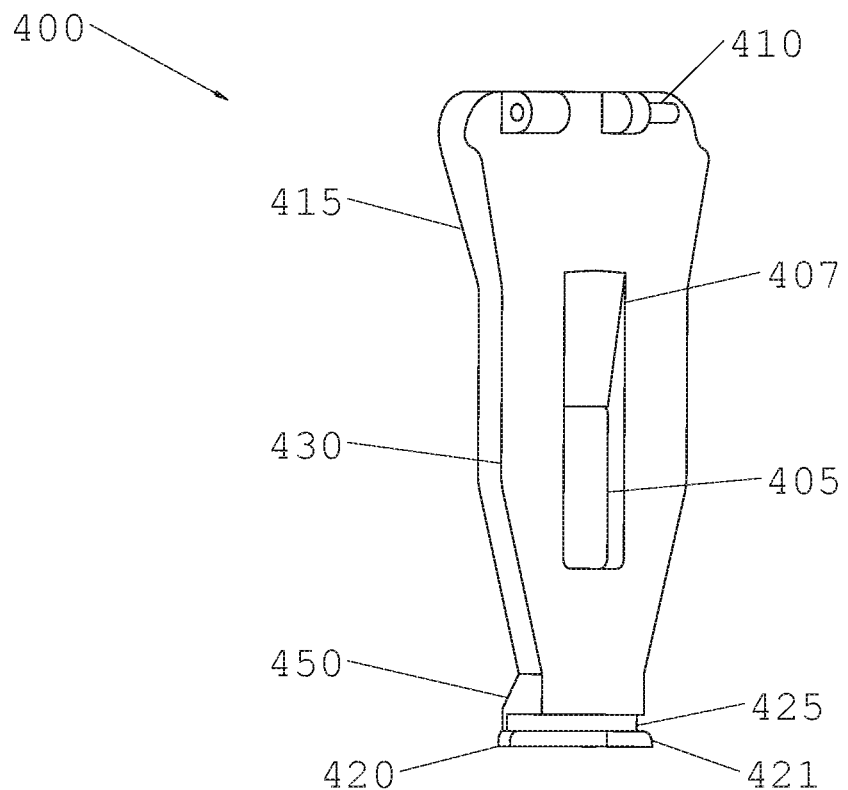
FIG. 11 is an inside view of the left insertion tool piece.

FIGS. 10 and 11 illustrate a left insertion tool piece. In this embodiment, left insertion tool piece 400 is a mirror image of right insertion tool piece 300. Features on left insertion tool piece 400 are equivalent in function to 300. Left insertion tool piece 400 consists of body 415, slider slot 405, slider slot lock 406, hinge 410, and additional features described below. Slider slot 405 is a window or hole in left insertion tool piece 400 that fits the dimensions of insertion tool slider 200. Slider slot lock 406 is a recessed area in left insertion tool piece 400 that also fits the dimensions of insertion tool slider 200, but in addition will allow slot 205 of insertion tool slider 200 to lock in place. This will be evident in subsequent drawings. Hinge 410 is configured to mate with a corresponding hinge on a right insertion tool piece 300, described in a previous drawing. Body 415 is designed to provide structural rigidity as well as ergonomic shape for a physician to hold. Left insertion tool piece 400 includes jaw 450 that is adapted to interface with an implant 1 at bridge 20 and legs 5 and 7. In particular, jaw 450 includes projections 420 and 421 that contact implant 1 at legs 5 and 7, respectively. Jaw 450 includes left insertion tool slot 425, which is only visible in FIG. 11 (inside view of the left insertion tool piece). Left insertion tool slot 425 is designed to match the shape of bridge 20 when implant 1 resides in its first position 100. Left insertion tool ramp 407, which is also only visible in FIG. 11, is a ramped section of a piece 400 that will be shown later to interface with the insertion tool slider 200. Finally, left insertion tool surface 430 is a surface that can mate with a second half of an insertion tool when it is in its assembled position.

Figure 12:
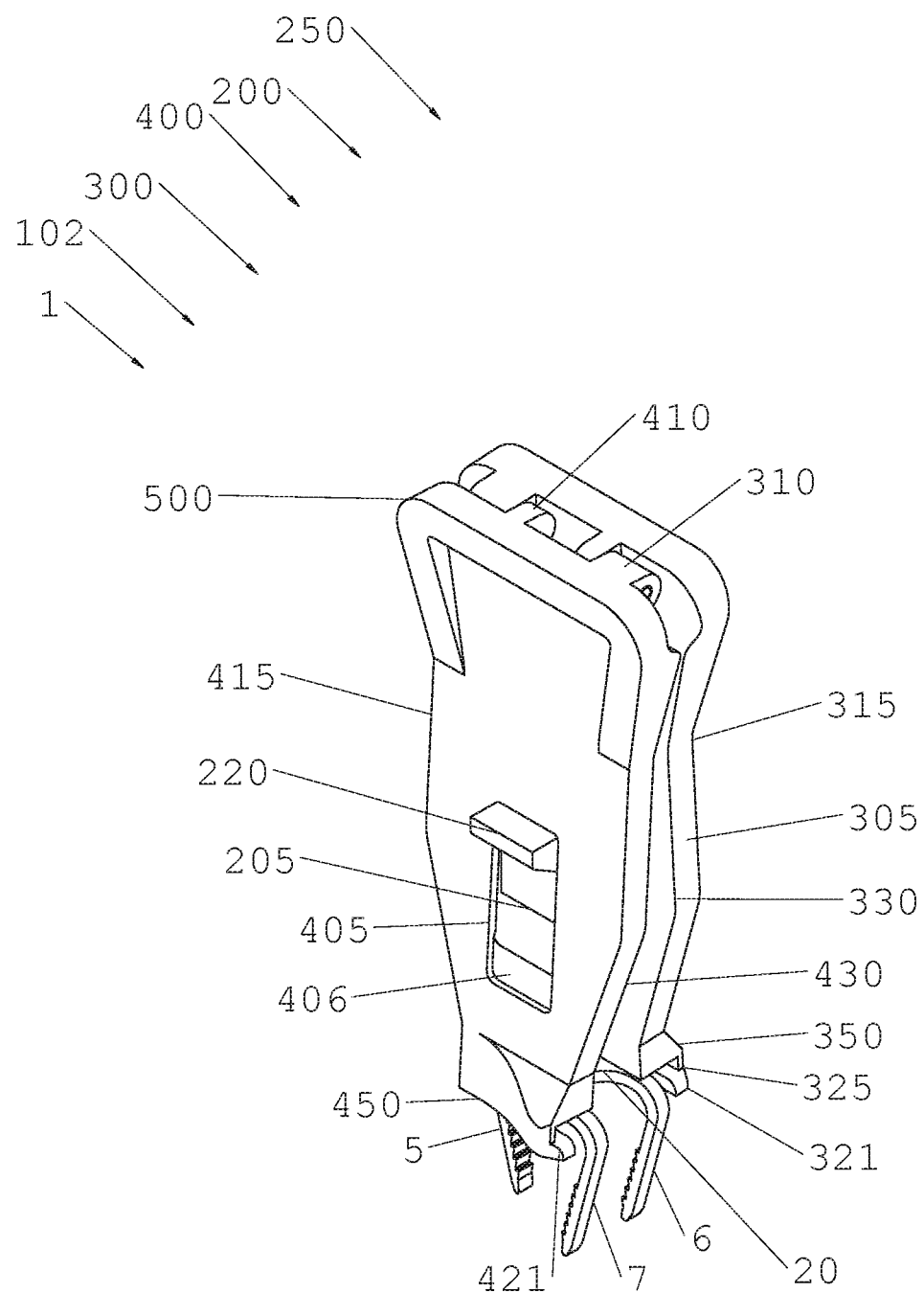
FIG. 12 is a perspective view illustrating the insertion tool assembly after release of the implant.
Figure 13:
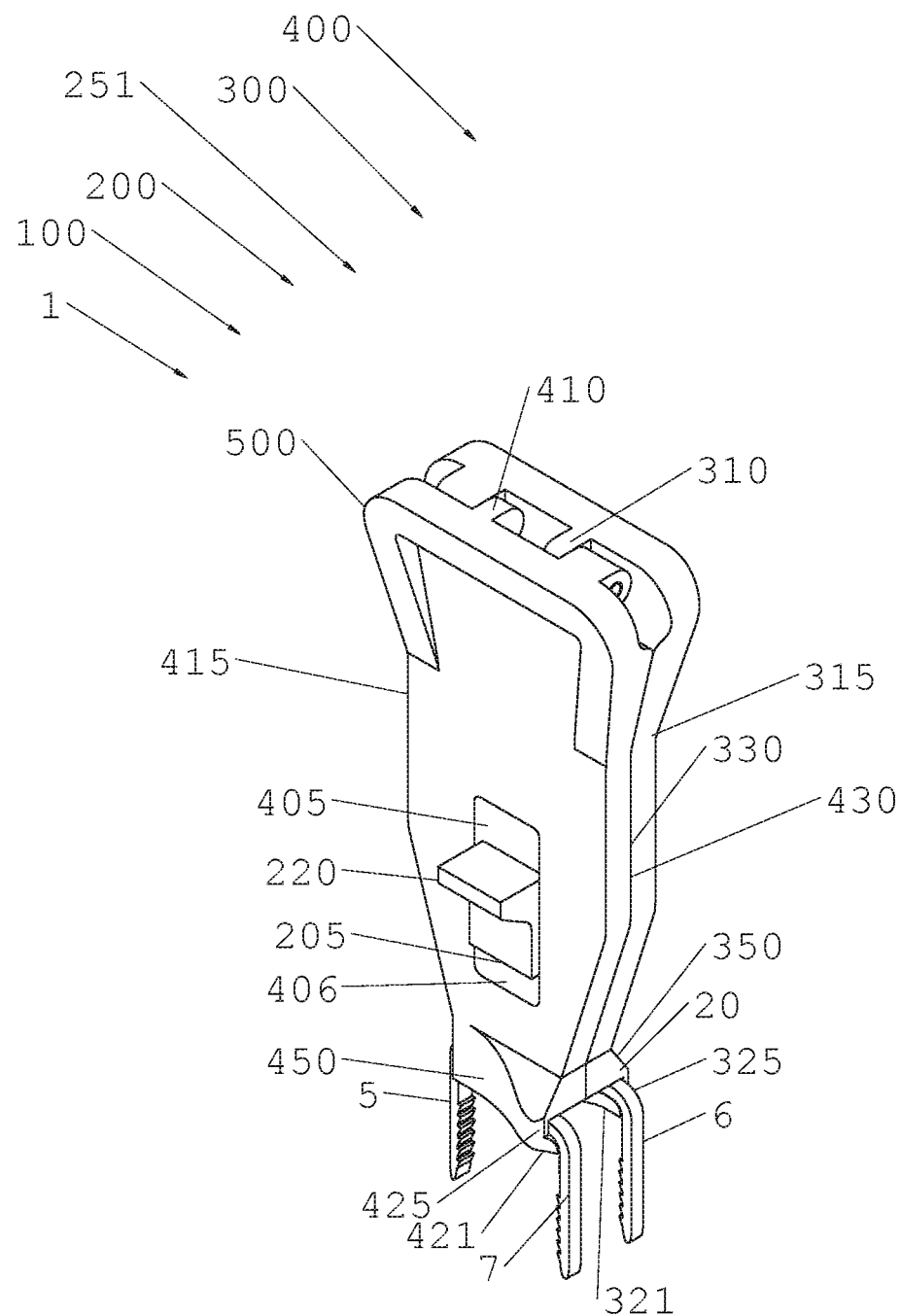
FIG. 13 is a perspective view illustrating the insertion tool assembly after unlocking the implant.
Figure 14:
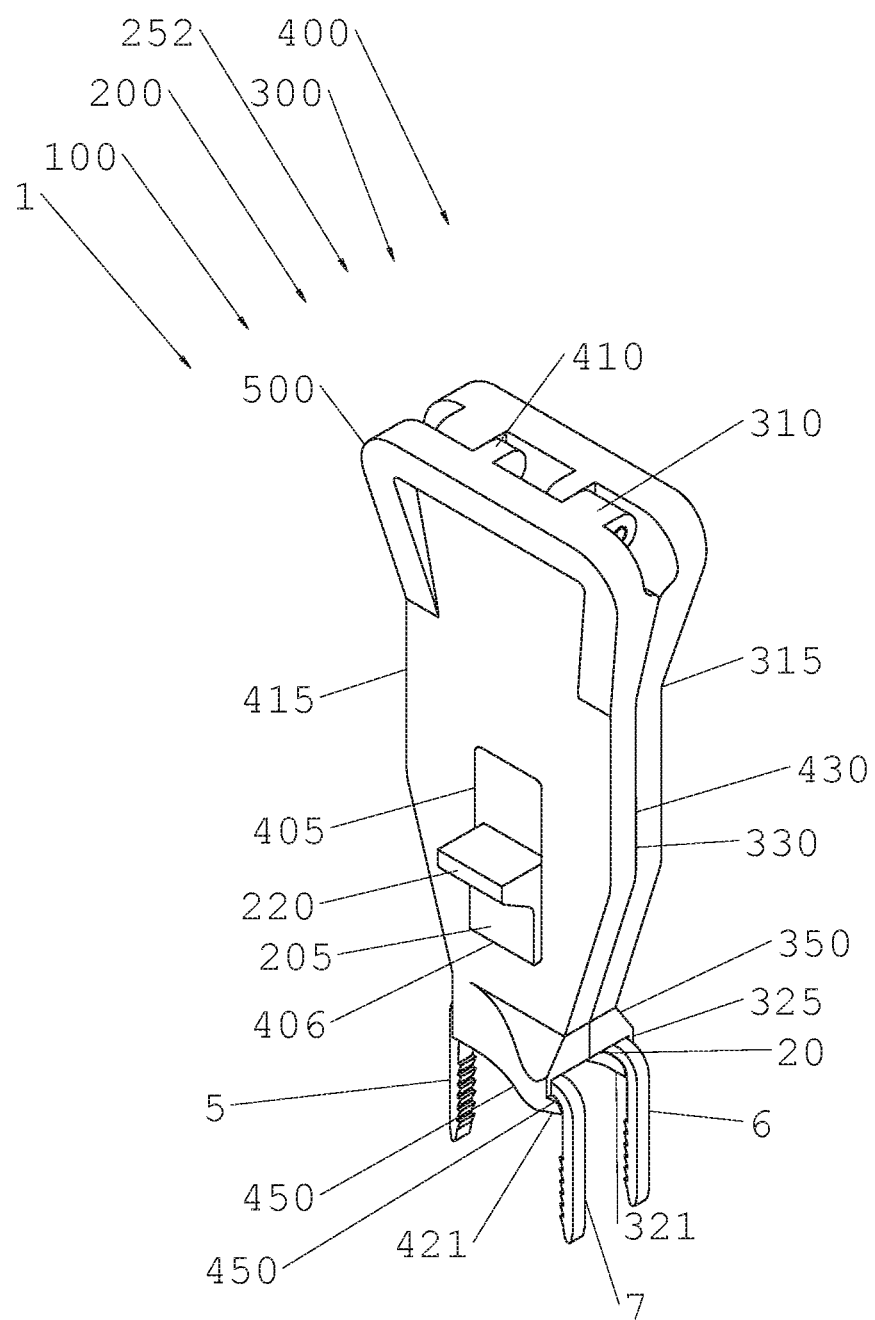
FIG. 14 is a perspective view illustrating the insertion tool assembly with the implant in a locked position.

FIGS. 12 through 14 illustrate how the insertion tool and implant can be used by a physician. FIG. 12 illustrates an insertion tool assembly in final shape 250. FIG. 12 illustrates the implant 1 of a second embodiment in a second position 102. Implant 1 is in the position of being released from insertion tool assembly 500. Shape 250 corresponds to the position of insertion tool assembly 500 just as it releases implant 1 after insertion into bone. Insertion tool assembly 500 consists of right insertion tool piece 300, left insertion tool piece 400, and insertion tool slider 200. Hinges 310 and 410 on right and left insertion tool pieces 300 and 400 interfaces with each other so that insertion tool assembly 500 stays together as one unit. Insertion tool slider 200 fits in between insertion tool pieces 300 and 400, with separator 206 and ramps 210 and 211 pointing upwards towards hinges 310 and 410, and slot 205 pointing downwards towards implant 1. Finger grips 220 and 221 project out through slider slots 305 and 405. In shape 250, finger grips 220 and 221 have been used by a physician to pull up on insertion tool slider 200, which causes the ramps 210 and 211 of insertion tool slider 200 to engage ramps 307 and 407 of right insertion tool piece 300 and left insertion tool piece 400, such that insertion tool slider 200 acts as a wedge that forces right and left insertion tool pieces 300 and 400 apart at the bottom while they remain connected by hinges 310 and 410. In shape 250, it is seen that finger grips 220 and 221 are near the top of slider slots 305 and 405. Also, in shape 250, jaws 350 and 450 are open such that implant 1 is not disposed in slots 325 and 425, projections 320 and 420 are separated and not engaged with implant 1, and projections 321 and 421 do not engage with implant 1, thus allowing insertion tool assembly 500 to be removed from implant 1 after implant 1 is in bone.

FIG. 13 illustrates the insertion tool in intermediate shape 251. FIG. 13 shows implant 1 in a first position 100, with legs 5, 6, and 7 parallel to each other. In shape 251, implant 1 is in the position of being on the verge of release from insertion tool assembly 500. Shape 251 corresponds to the position of insertion tool assembly 500 before it releases implant 1 after insertion into bone. In shape 251, finger grips 220 and 221 have been used by a physician to partially pull up on insertion tool slider 200, such that slot 205 no longer engages slider slot locks 306 and 406, however, separator 206 and ramps 210 and 211 have not yet forced insertion tool pieces 300 and 400 to separate. Insertion tool 500 in shape 251 is thus in an intermediate position where the physician has unlocked the two halves of the insertion tool pieces but not yet separated them. In shape 251, it is seen that finger grips 200 and 221 are near the middle of slider slots 305 and 405. Also in shape 251, jaws 350 and 450 are closed to engage with implant 1 in its first position 100. In particular, slots 325 and 425 receive therein the bridge 20 of the implant 1, projections 320 and 420 come together and engage leg 5 to mechanically constrain leg 5 in the parallel position, and projections 321 and 421 engage a respective leg 6 and 7 to mechanically constrain legs 6 and 7 in the parallel position.

FIG. 14 illustrates the insertion tool assembly in initial shape 252. FIG. 14 shows implant 1 in a first position 100, with legs 5, 6, and 7 parallel to each other. In shape 252, implant 1 is firmly held and locked by insertion tool assembly 500 with legs 5, 6, and 7 parallel. Shape 252 corresponds to the position of insertion tool assembly 500 when a physician is preparing to use implant 1, but it has not yet been placed into bone. In shape 252, finger grips 220 and 221 have not yet been used by a physician, and slot 205 engages slider slot locks 306 and 406, keeping slider slot locks 306 and 406 together and thus keeping insertion tool pieces 300 and 400 together. Insertion tool 500 in shape 252 is thus the initial position where the physician has not yet unlocked or separated the two halves of the insertion tool pieces. In shape 252, it is seen that finger grips 200 and 221 are near the bottom of slider slots 305 and 405. Also, in shape 252, jaws 350 and 450 are closed to engage with implant 1 in its first position 100. In particular, slots 325 and 425 receive therein the bridge 20 of the implant 1, projections 320 and 420 come together and engage leg 5 to mechanically constrain leg 5 in the parallel position, and projections 321 and 421 engage a respective leg 6 and 7 to mechanically constrain legs 6 and 7 in the parallel position. While the preferred embodiment discloses jaw 350 including projection 320 and jaw 450 including projection 420, one of ordinary skill in the art will recognize that a single projection on either jaw 350 or 450 may be used.

Figure 15:
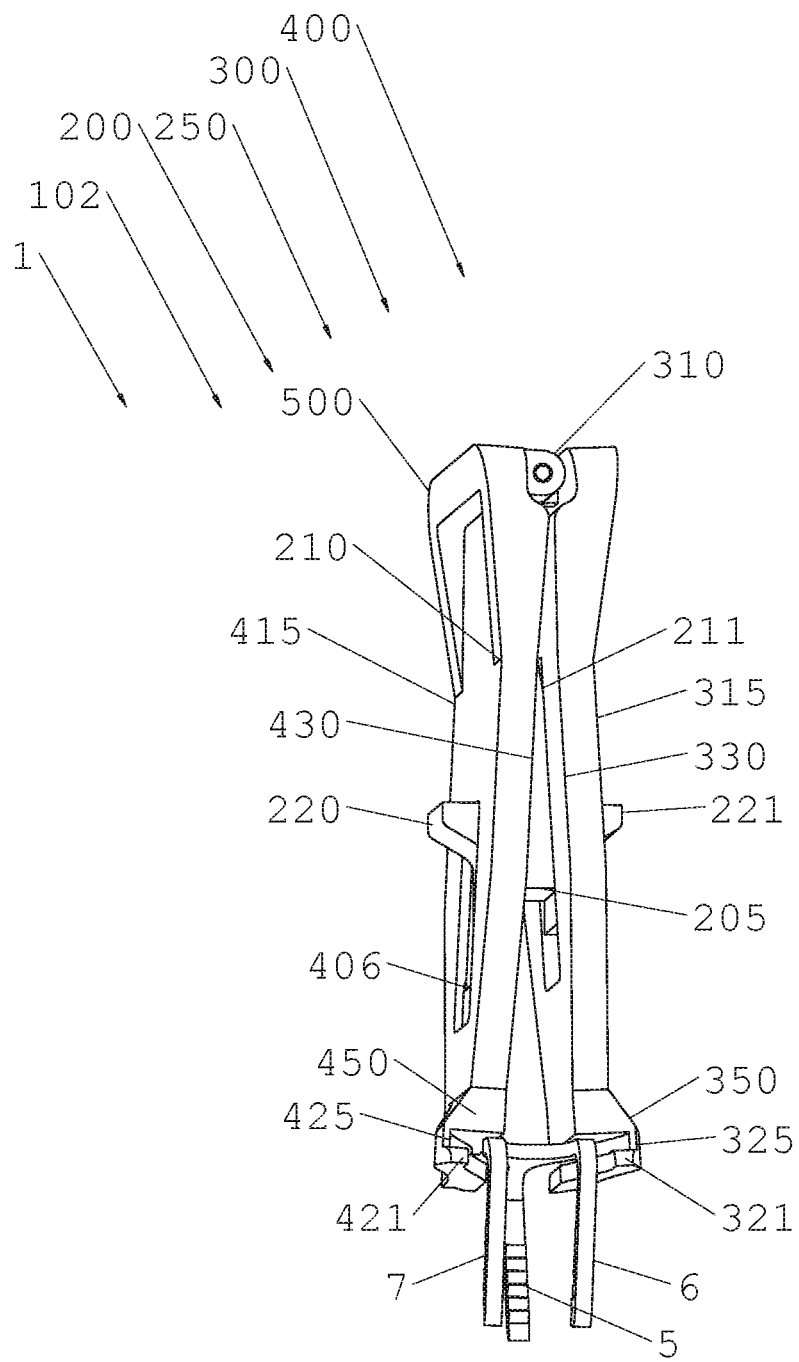
FIG. 15 is a side view of the insertion tool assembly after release of the implant.

FIG. 15 illustrates the insertion tool assembly after release of an orthopedic implant. Insertion tool assembly 500 is in its final shape 250 with right and left insertion tool pieces 300 and 400 separated at the bottom with jaws 350 and 450 in their open position, but still held together by hinges 310 and 410 at the top. In this view, it can be seen that insertion tool assembly 500 is free to be removed from implant 1 because jaws 350 and 450 are no longer engaging implant 1. In addition, slot 205 can be seen to no longer be engaged with slot locks 306 and 406, which is what permits insertion tool pieces 300 and 400 to separate from each other. What cannot be seen in this figure, but is occurring nonetheless, is that a physician has pulled up on finger grips 220 and 221, causing ramps 210 and 211 to engage corresponding ramps 307 and 407 on right and left insertion tool pieces 300 and 400, and ramps 210 and 211 have then acted as a wedge to force the two insertion tool pieces apart.

Figure 16A:
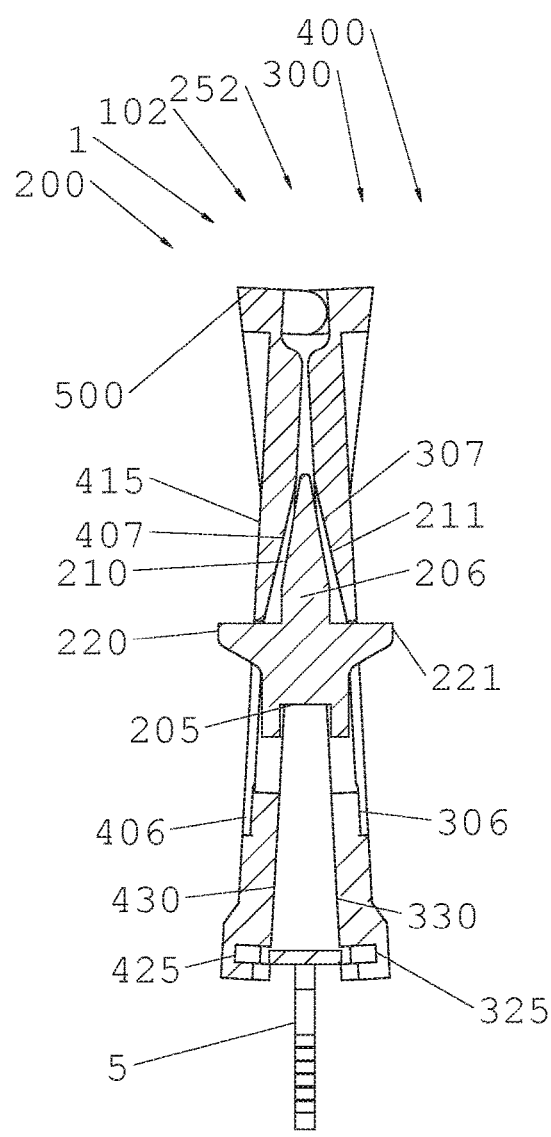
FIG. 16A is a section view taken along line A-A of FIG. 16B illustrating the insertion tool assembly after release of the implant.
Figure 16B:
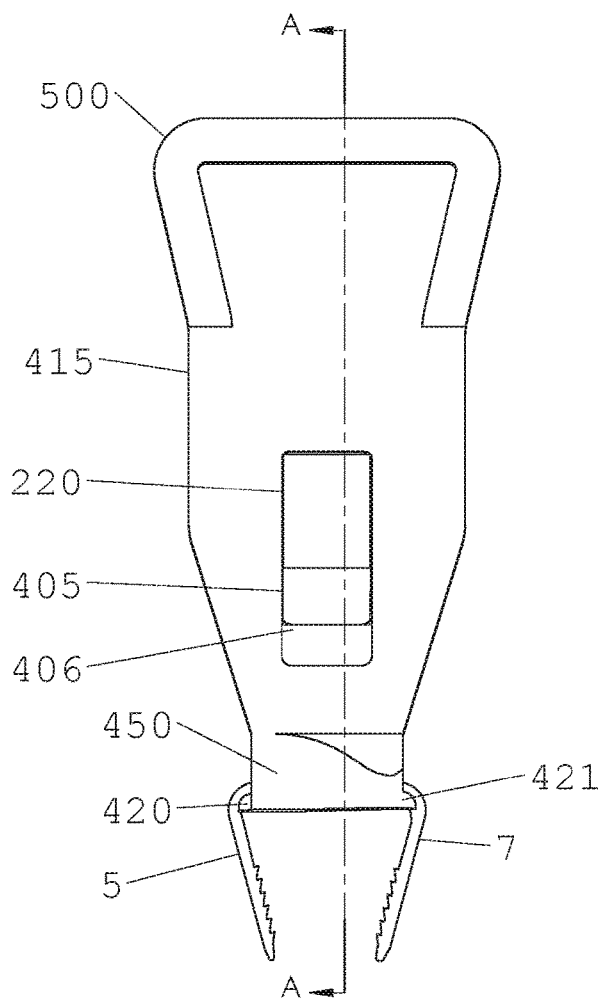
FIG. 16B is a side view illustrating the insertion tool assembly after release of the implant.

FIGS. 16A and 16B illustrate the insertion tool assembly components after release of an orthopedic implant. This corresponds to final shape 250 of insertion tool 500. In FIG. 16A, the functioning of insertion tool slider 200 are apparent. Finger grips 220 and 221 have been used by the physician to pull up on slider 200, which releases slot 205 from restraining locks 306 and 406. In addition, pulling upon slider 200 has caused ramps 210 and 211 on slider 200 to engage ramps 307 and 407 on insertion tool pieces 300 and 400, wedging the two pieces apart at the bottom such that jaws 350 and 450 are in their open position. This action causes slots 325 and 425 to release implant 1 so that its legs 5, 6, and 7 can create compression in bone, and insertion tool assembly 500 can be lifted away from implant 1.

Figures 17A, 17B:
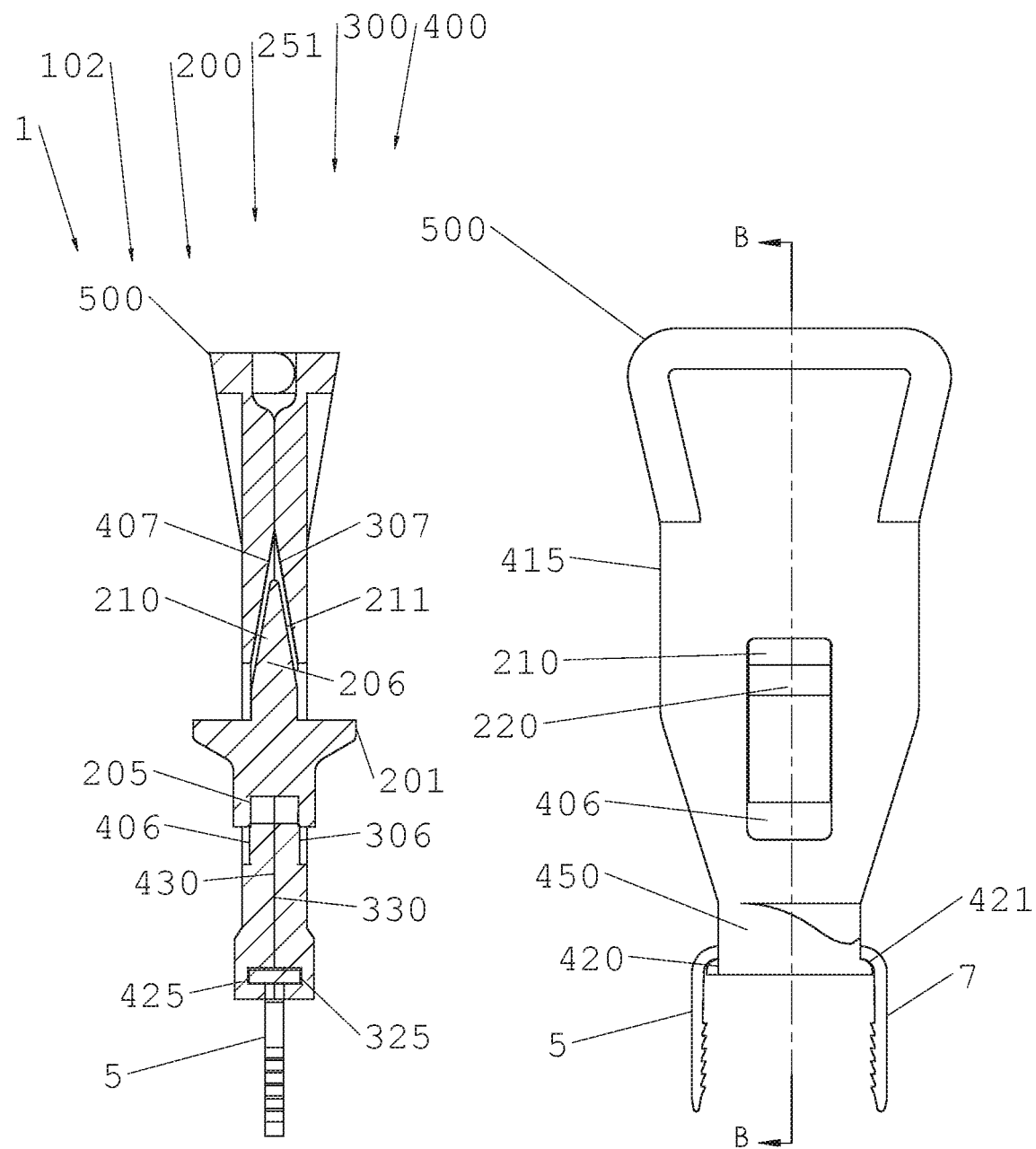
FIG. 17A is a section view taken along line B-B of FIG. 17B illustrating the insertion tool assembly after unlocking the implant.
FIG. 17B is a side view illustrating the insertion tool assembly after unlocking the implant.

Similarly, FIGS. 17A and 17B illustrate the insertion tool assembly components after unlocking an orthopedic implant but before separating the two halves of insertion tool assembly 500. This corresponds to shape 251 for insertion tool 500. The function of insertion tool slider 200 is apparent in FIG. 17A. A physician has partially raised finger grips 220 and 221, such that slot 205 no longer engages slider lock slots 306 and 406. However, ramps 210 and 211 are not yet wedging the two halves of insertion tool assembly 500 apart. This leaves insertion tool assembly 500 in an intermediate shape where the jaws 350 and 450 are closed to constrain implant 1, but it is on the verge of releasing implant 1. Projections 320, 321, 430, and 421 contact respective legs 5, 6, and 7 of implant 1 such that legs 5, 6, and 7 are still parallel and implant 1 is in first position 100.

Figure 18A:
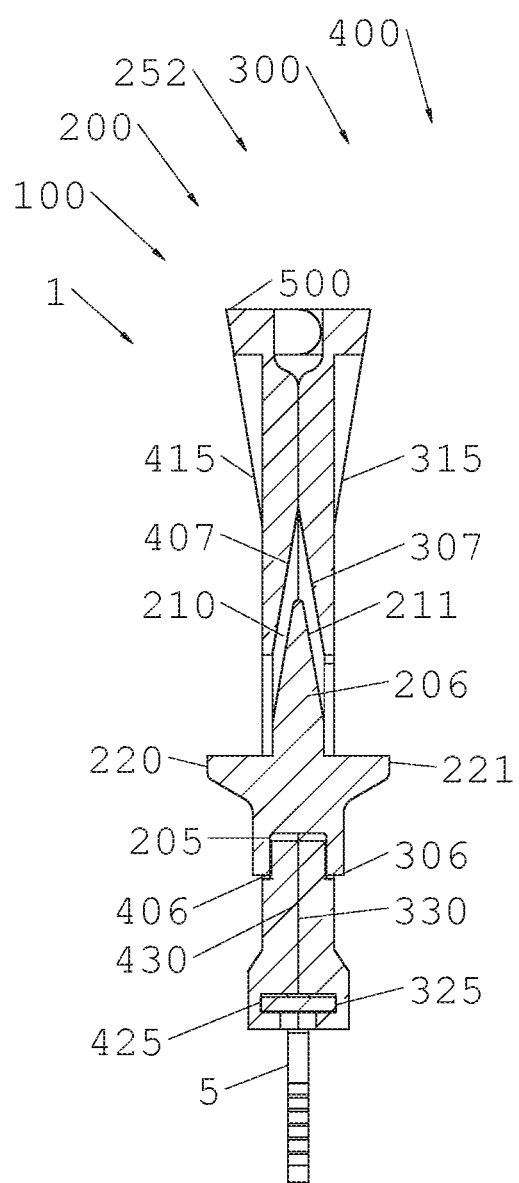
FIG. 18A is a section view taken along line C-C of FIG. 18B illustrating the insertion tool in the locked position.
Figure 18B:
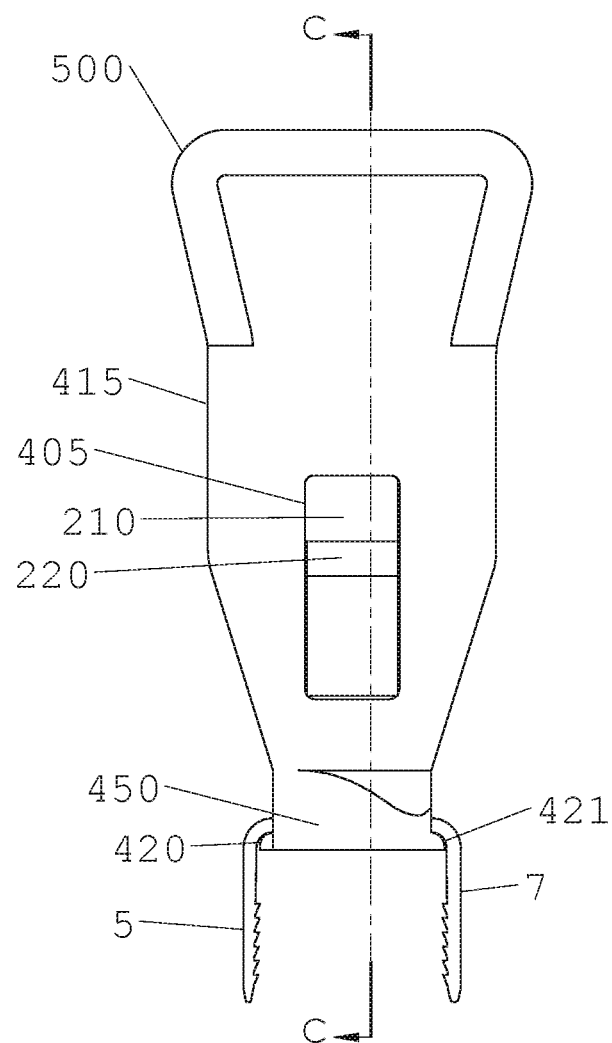
FIG. 18B is a side view illustrating the insertion tool assembly in the locked position.

FIGS. 18A and 18B illustrate the orthopedic implant 1 in the locked position held by insertion tool assembly. Implant 1 is in first position 100, and insertion tool 500 is in shape 252. Slider 200 has not been used by a physician, and therefore is in its locked downward position. Slot 205 constrains slider lock slots 306 and 406. Right and left insertion tool slots 325 and 425 include bridge 20 received therein and projections 320, 321, 430, and 421 contact respective legs 5, 6, and 7 to constrain legs 5, 6, and 7 of implant 1 in the parallel position. Right insertion tool surface 330 and left insertion tool surface 430 are touching in these figures.

Figure 19:
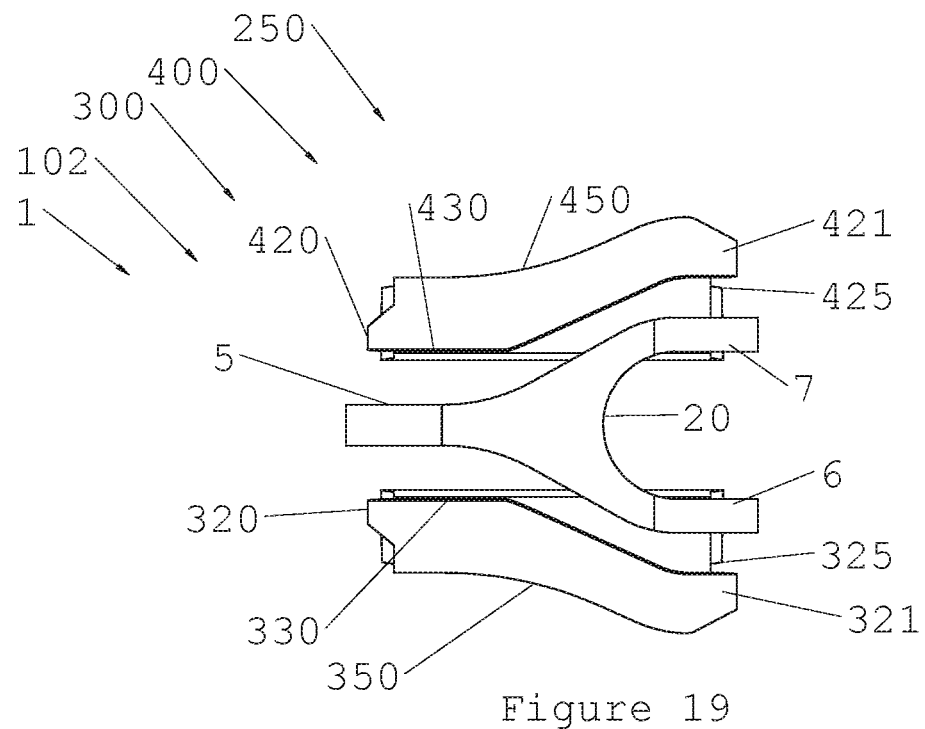
FIG. 19 is a bottom view of the insertion tool assembly after release of the implant.

FIG. 19 illustrates the insertion tool assembly after release of the orthopedic implant. This corresponds to implant 1 in second position 102, and insertion tool assembly 500 in final shape 250. Note that slots 325 and 425 on right and left insertion tool pieces are not engaging implant 1, and thus projections 320, 321, 430, and 421 are not constraining legs 5, 6, and 7 in their parallel positions.

Figure 20:
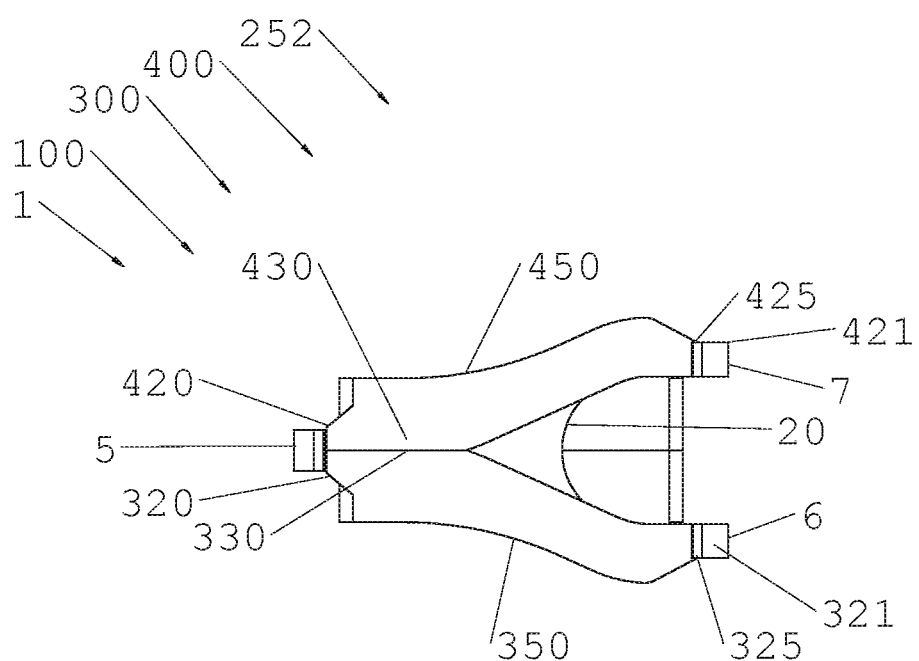
FIG. 20 is a bottom view of the insertion tool assembly with the implant in the locked position.

FIG. 20 illustrates the orthopedic implant in the locked position. This corresponds to implant 1 in first position 100, and insertion tool assembly 500 in initial shape 252. Surfaces 330 and 430 are touching, and slots 325 and 425 engage bridge 20 of implant 1 and projections 320, 321, 430, and 421 constrain legs 5, 6, and 7 in their parallel positions.

It can also be seen that the foregoing steps represent a method for inserting an orthopedic implant. In particular, an insertion tool assembly 500 holds and constrains an orthopedic implant 1 in an insertion shape, such that the legs of implant 1 can be inserted into drill holes in bone. A physician drills holes in bone at the proper distance from each other. The physician inserts the implant legs into bone by holding the insertion tool assembly. At the desired time, the physician pulls up on the insertion tool assembly slider, which unlocks the two halves of the insertion tool assembly. Continuing to pull up on the slider causes the two halves to separate due to the wedge action of the slider, and thus releases the implant.

Although the present invention has been described in terms of the foregoing preferred embodiments, including the insertion instrument and its components, the method of use of the insertion instrument and its various components, the method of controllably releasing the implant, the combination of the implant and its interaction with the insertion instrument, and other ideas presented herein, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A method of holding a shape memory implant until delivery of the shape memory implant into tissue or bone, comprising:
   providing a shape memory implant, comprising a bridge interconnecting first, second, and third legs, whereby the shape memory implant is movable between a first shape wherein the first leg is non-parallel with the second and third legs and a second shape wherein the first leg is substantially parallel with the second and third legs, further whereby the shape memory implant is provided in its second shape;
   moving a slider of an implant insertion device whereby the slider inserts between a first insertion tool piece hingedly connected to a second insertion tool piece such that the first and second insertion tool pieces separate thereby opening the implant insertion device to receive the shape memory implant therein;
   placing the shape memory implant between a first jaw of the first insertion tool piece and a second jaw of the second insertion tool piece;
   moving the slider of the implant insertion device whereby the slider permits closure of the first and second jaws of the first and second insertion tool pieces such that:
     a first tool slot in the first jaw and a second tool slot in the second jaw each receive therein a portion of the bridge of the shape memory implant,
     the first jaw engages the first and second legs to maintain the shape memory implant in its second shape wherein the first leg is substantially parallel with the second and third legs, and
     the second jaw engages at least the third leg; and
   moving the slider of the implant insertion device whereby the slider engages the first and second insertion tool pieces to lock the first and second jaws closed about the shape memory implant in its second shape.

2. The method of holding the shape memory implant until the delivery of the shape memory implant into tissue or bone according to claim 1, further comprising:
   using the implant insertion device to deliver into tissue or bone the shape memory implant in its second shape wherein the first leg is substantially parallel with the second and third legs;
   moving the slider of the implant insertion device whereby the slider disengages from the first and second insertion tool pieces to unlock the first and second jaws;
   moving the slider of the implant insertion device whereby the slider inserts between the first and second insertion tool pieces such that the first and second insertion tool pieces separate thereby releasing the shape memory implant from the first and second jaws; and
   the shape memory implant moves from its second shape wherein the first leg is substantially parallel with the second and third legs to its first shape wherein the first leg is non-parallel with the second and third legs.

* * * * *